US 9,220,556 B2

(12) United States Patent
Lalonde et al.

(10) Patent No.: US 9,220,556 B2
(45) Date of Patent: Dec. 29, 2015

(54) BALLOON DESIGN TO ENHANCE COOLING UNIFORMITY

(75) Inventors: Jean-Pierre Lalonde, Candiac (CA); Scott W. Davie, Beaconsfield (CA); Dan Wittenberger, L'Île-Bizard (CA)

(73) Assignee: Medtronic CryoCath LP, Toronto, Ontario (CA)

( * ) Notice: Subject to any disclaimer, the term of this patent is extended or adjusted under 35 U.S.C. 154(b) by 953 days.

(21) Appl. No.: 13/360,430

(22) Filed: Jan. 27, 2012

(65) Prior Publication Data

US 2013/0197499 A1  Aug. 1, 2013

(51) Int. Cl.
 *A61B 18/00* (2006.01)
 *A61B 18/02* (2006.01)
 *A61B 18/14* (2006.01)
 *A61B 19/00* (2006.01)

(52) U.S. Cl.
 CPC ............. *A61B 18/02* (2013.01); *A61B 18/1492* (2013.01); *A61B 2018/0022* (2013.01); *A61B 2018/00255* (2013.01); *A61B 2018/00375* (2013.01); *A61B 2018/00577* (2013.01); *A61B 2018/00791* (2013.01); *A61B 2018/00994* (2013.01); *A61B 2018/0212* (2013.01); *A61B 2018/0268* (2013.01); *A61B 2019/464* (2013.01)

(58) Field of Classification Search
 CPC ..................... A61B 18/02; A61B 2018/00005; A61B 2018/0022; A61B 2018/00232; A61B 2018/0025; A61B 2018/00255; A61B 2018/00261
 See application file for complete search history.

(56) References Cited

U.S. PATENT DOCUMENTS

| 5,902,299 | A | 5/1999 | Jayaraman | |
|---|---|---|---|---|
| 8,012,147 | B2 | 9/2011 | Lafontaine | |
| 2002/0045893 | A1* | 4/2002 | Lane et al. | 606/21 |
| 2002/0072738 | A1* | 6/2002 | Edwards et al. | 606/41 |
| 2002/0151880 | A1* | 10/2002 | Lafontaine | 606/21 |
| 2005/0203597 | A1* | 9/2005 | Yamazaki et al. | 607/98 |
| 2006/0030843 | A1 | 2/2006 | Lane et al. | |
| 2009/0182317 | A1* | 7/2009 | Bencini | 606/21 |
| 2009/0182318 | A1* | 7/2009 | Abboud et al. | 606/21 |

(Continued)

FOREIGN PATENT DOCUMENTS

| CA | 2443479 A1 | 10/2002 |
|---|---|---|
| CA | 2667101 A1 | 4/2008 |

(Continued)

OTHER PUBLICATIONS

CIPO, PCT/CA2012/001167, Mar. 8, 2013 International Search Report, pp. 1-3.
CIPO, PCT/CA2012/001167, Mar. 8, 2013 Written Opinion, pp. 1-4.

*Primary Examiner* — Theodore Stigell
*Assistant Examiner* — Natasha Patel
(74) *Attorney, Agent, or Firm* — Christopher & Weisberg, P.A.

(57) ABSTRACT

A device, system, and method for enhancing cooling uniformity and efficiency of cryogenic fluids and providing a treatment element the shape of which can be adjusted for multiple purposes. The device may include a balloon catheter and fluid dispersion element, the fluid dispersion element directing the flow of coolant from a fluid injection element the interior wall of the balloon. The method of changing the shape of the treatment element may include retracting and extending a shaft to which the distal neck of a balloon is coupled, so that the balloon goes from a first shape to a second shape.

24 Claims, 8 Drawing Sheets

(56) References Cited

U.S. PATENT DOCUMENTS

2010/0125266 A1* 5/2010 Deem et al. .................. 606/21
2011/0263921 A1* 10/2011 Vrba et al. .................... 600/3
2012/0136418 A1* 5/2012 Buckley et al. .............. 607/105

FOREIGN PATENT DOCUMENTS

| CA | 2786787 A1 | 8/2011 |
|----|------------|--------|
| WO | 0047118 A1 | 8/2000 |
| WO | 2007053209 A1 | 5/2007 |

\* cited by examiner

BALLOON DESIGN TO ENHANCE COOLING UNIFORMITY

CROSS-REFERENCE TO RELATED APPLICATION n/a

STATEMENT REGARDING FEDERALLY SPONSORED RESEARCH OR DEVELOPMENT n/a

FIELD OF THE INVENTION

The present invention relates to a method and system for enhancing cooling uniformity and efficiency of cryogenic fluids and providing a treatment element having a shape that can be adjusted for multiple purposes.

BACKGROUND OF THE INVENTION

Cryoablation therapy is a technique that uses freezing to locally destroy or alter body tissue, such as a tumor, cardiac tissue associated with arrhythmia, or diseased or congenitally abnormal tissue. Surgical cryoprobes and cryoablation catheters are typically used to perform this technique, and may generally include a power source, a coolant source, and one or more treatment elements. Commonly used cryoablation treatment elements include expandable elements (for example, balloons) through which cryogenic fluid, such as a phase-change coolant, circulates. The temperature of phase-change coolants is lowered via the Joule-Thomson effect, which occurs when the coolant expands within the treatment element.

When the treatment elements of the catheter must chill tissue to below freezing, the coolant itself must attain a substantially lower temperature. Although phase-change coolants can reach sufficient temperatures at expansion, coolant temperature rapidly rises after expansion within the treatment element. For example, a small coolant-filled balloon must overcome the heat of blood flow and surrounding tissue to maintain freezing temperatures. Typically, this problem is solved by injecting coolant into the treatment element at high flow rates and pressures, with rapid removal and replacement with fresh coolant. However, conditions of patient safety must be considered. When high pressures are be required to circulate sufficient coolant through the catheter body to its tip and back, and the overall design of a catheter must be such that fracture of the catheter or leakage of the coolant either does not occur, or if it occurs, is harmless. Further, for an endovascular catheter construction, the presence of the coolant and circulation system should not substantially impair the flexibility or maneuverability of the catheter tip and body.

Patient safety must also be considered when choosing the shape of the cryoablation treatment element. For example, a balloon catheter should be sized and shaped to adequately occlude an area of the body such as the pulmonary vein. However, ablating tissue with a balloon shape that is optimal for occlusion, such as a teardrop shape, may increase the risk of the balloon getting deep in the vein and leading to pulmonary vein stenosis or other vascular damage. Additionally in order to apply a spherical balloon 'head-on' against a flat structure like the posterior wall, the distal "neck" of the balloon will need to be withdrawn sufficiently to allow contact by the rest of the balloon.

Accordingly, it would be desirable to provide a cryoablation device and system that would more efficiently circulate coolant through the treatment element proximate the target tissue without necessitating potentially dangerous high pressures and flow rates. Additionally, it would be desirable if this cryoablation device and system further included the ability to change the shape of the treatment element to enable a single device to serve multiple purposes.

SUMMARY OF THE INVENTION

The present invention advantageously provides a device, system, and method for not only enhancing cooling uniformity and efficiency of cryogenic fluids, but also changing the shape of a cryoablation treatment element to serve multiple purposes. The device may comprise: a cooling chamber including an interior wall and an exterior wall; a coolant delivery element disposed within the cooling chamber; and a coolant distribution element disposed within the cooling chamber that guides coolant delivered from the coolant delivery element toward the interior wall of the cooling chamber. The cooling chamber may be a balloon. The coolant distribution element may be a membrane disposed within the cooling chamber so as to divide the cooling chamber into a first portion and a second portion, the coolant delivery element being within the first portion and the membrane allowing transit of coolant from the first portion to the second portion. Further, the membrane meters transit of coolant from the first portion to the second portion, and may be at least one of: gas permeable; liquid permeable; and combination thereof. Further, the membrane includes a plurality of apertures. The apertures may be located proximate the interior wall of the cooling chamber. Further, the membrane may includes a first edge and a second edge, the first edge being in contact with a portion of the interior wall of the cooling chamber. The first edge may be affixed to the interior wall of the cooling chamber.

Alternatively, the coolant distribution element may be a second balloon disposed within the cooling chamber. The coolant distribution element may be disposed within the cooling chamber so as to divide the coolant chamber into a first portion within the second balloon and a second portion between the cooling chamber and second balloon, and the second balloon meters transit of coolant from the first portion to the second portion. The coolant delivery element may be disposed within the second balloon, and the second balloon may include a plurality of apertures. Alternatively, the coolant delivery element may be disposed between the balloon and the second balloon, the second balloon being coolant-impermeable.

The device may further comprise: a first shaft having a proximal end, a distal end, and a first lumen extending therebetween, the proximal neck of the balloon being coupled to the distal end of the first shaft; and a second shaft slidably disposed within the first lumen and having a distal end, the distal neck of the balloon being coupled to the distal end of the second shaft. The second edge of the membrane may be in contact with the second shaft, the second shaft being slidably disposed through the membrane. The second shaft may include the coolant delivery element. Further, the second shaft may be slidably movable with respect to the coolant delivery element. The balloon may have the first shape when the second shaft is in an extended position, and the balloon has the second shape when the second shaft is in a retracted position. The distal neck of the balloon may be oriented outward and away from the expandable element when the balloon is in the first position, and the distal neck of the balloon may be oriented inward and within the first portion of the balloon when the balloon is in the second position.

Alternatively, the device may comprise: an expandable element including an interior wall, an exterior wall, an adjustable distal neck, and a fixed proximal neck; a fluid distribution membrane disposed within the expandable element so as to divide the expandable element into a first portion and a second portion, the membrane including a plurality of apertures proximate at least a portion of the interior wall that allow the transit of fluid from the first portion to the second portion; and a fluid injection element within the first portion, the expandable element having a first shape when the distal neck is oriented outward and away from the expandable element, and a second shape when the distal neck is oriented inward and within the expandable element.

The method may comprise: providing an expandable element having an interior wall and an exterior wall, a fluid distribution element disposed within the expandable element so as to divide the expandable element into a first portion and a second portion; injecting coolant through a fluid injection element within the first portion, the fluid distribution element guiding coolant toward the interior wall of the first portion, through the fluid distribution element, and into the second portion. The fluid distribution element may include a plurality of apertures proximate the inner wall of the expandable element, the apertures allowing for the metered transit of the fluid from the first portion to the second portion. The expandable element may have a fixed proximal neck and a distal adjustable neck, the distal neck being coupled to a slidably movable sheath, the expandable element having a first shape when the sheath is in an extended position and having a second shape when the sheath is in a retracted position.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION OF THE INVENTION

Figure 1A:
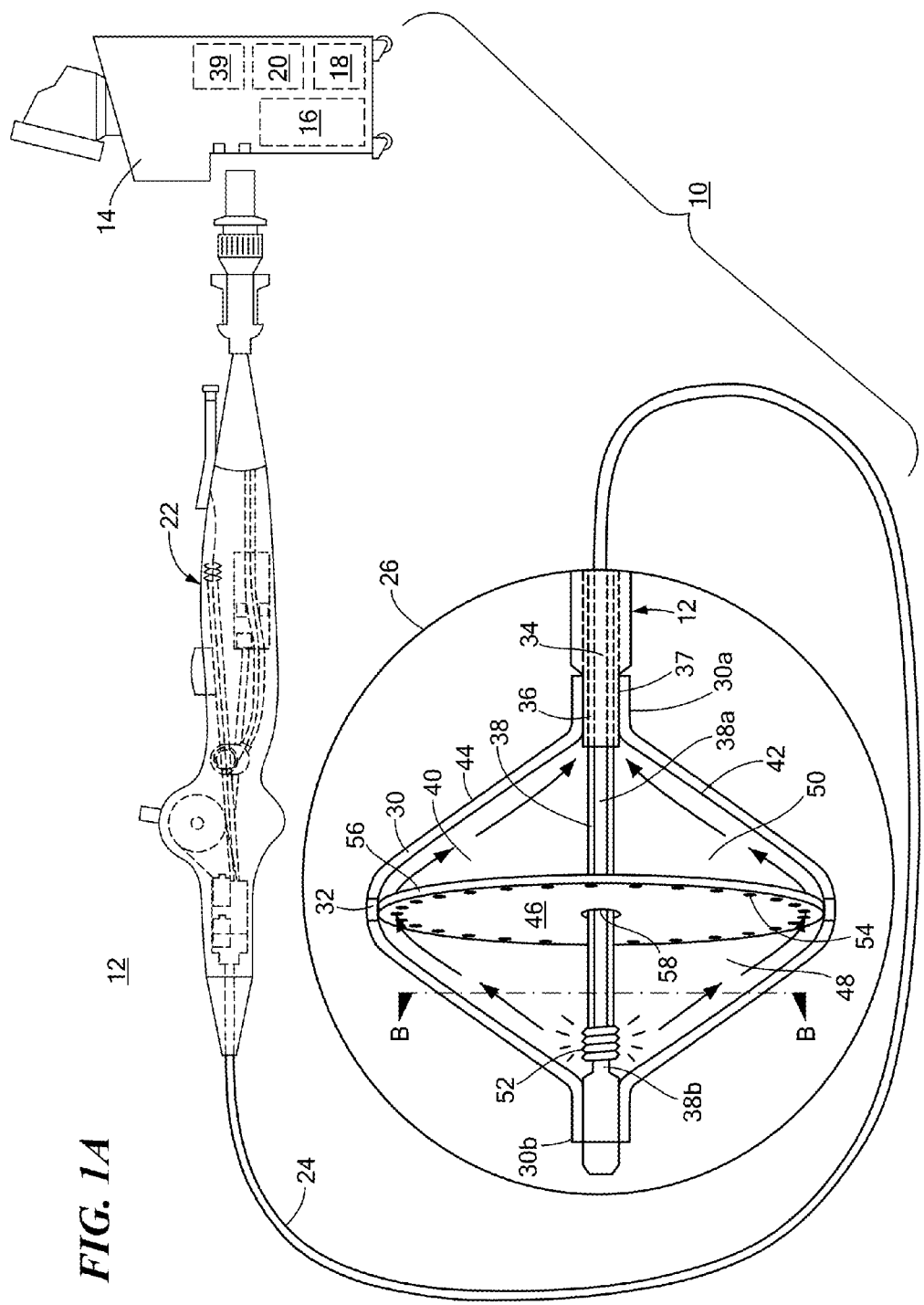
FIG. 1A shows a system including a first embodiment of a cryoablation treatment element.

Referring now to FIG. 1A, a system including a first embodiment of a cryoablation treatment element is shown. The system 10 generally includes a device 12 for treating tissue and a console 14 that houses various system controls. The system 10 may be adapted for both radiofrequency ablation (RFA) and cryoablation. The console 14 may include one or more of a coolant reservoir 16, coolant return reservoir 18, and RF generator 20, and may further include various displays, screens, user input controls, keyboards, buttons, valves, conduits, connectors, power sources, and computers for adjusting and monitoring system parameters.

Continuing to refer to FIG. 1A, the device 12 may be an ablation device generally including a handle 22, an elongate body 24 having a distal end 26 and one or more treatment elements. The handle 22 may include various knobs, levers, user control devices, input ports, outlet ports, connectors, lumens, and wires. The one or more treatment elements may be expandable elements such as balloons 30 (as shown in FIG. 1A). Further, the device may include one or more electrodes 32, such as when thermoelectric cooling and/or RF energy is used in addition to Joule-Thomson cooling. The elongate body 24 may further include one or more lumens, such as a main lumen 34, a fluid injection lumen 36 in fluid communication with the coolant reservoir 16, and a fluid return lumen 37 in fluid communication with the coolant return reservoir 18. In some embodiments, one or more other lumens may be disposed within the main lumen 34, and/or the main lumen 34 may function as the fluid injection lumen 36 or the fluid return lumen 37. If the device 12 also includes a thermoelectric cooler or RF electrodes, the elongate body 24 may include a lumen in communication with an RF generator 20 and/or a power source (not shown). Even if not shown in the other figures, the device 12 shown in, for example, FIGS. 2A, 3, 4, 5A, 7A, and 7B may also include these lumens 34, 36, 37.

Figure 7A:
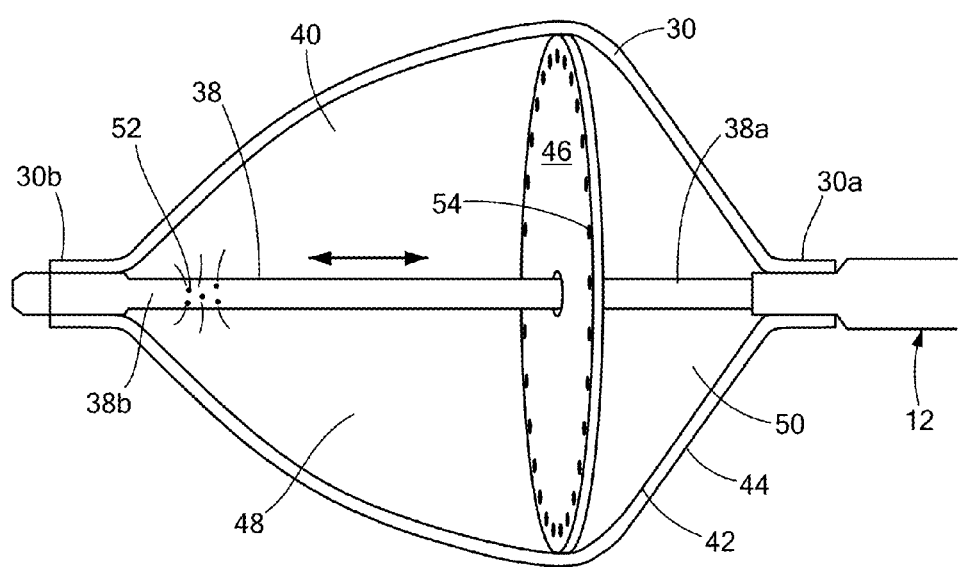
FIG. 7A shows a cross sectional view of a first embodiment of a shape-changing cryoablation treatment element having a first shape.
Figure 7B:
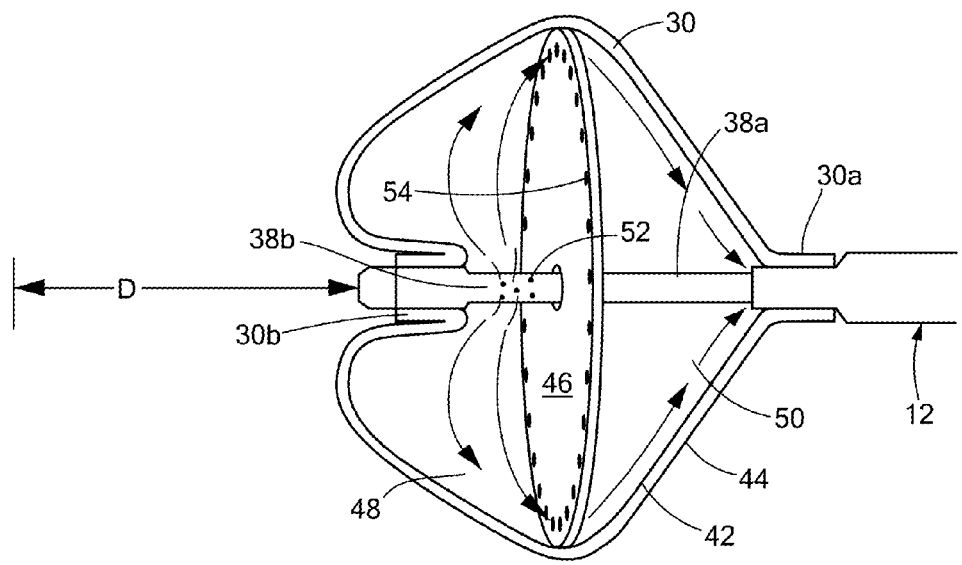
FIG. 7B shows a cross-sectional view of a first embodiment of a shape-changing cryoablation treatment element having a second shape.

The elongate body may further include a shaft 38 having a proximal end 38a and a distal end 38b, which may be slidably disposed within the main lumen 34 (as shown and described in FIGS. 7A and 7B). Generally, the shaft 38 is any substantially rigid shaft to which at least a portion of the treatment element (such as a balloon 30, as shown in FIG. 1A) may be attached, and may be a guidewire shaft. The coolant return reservoir 18 may be in fluid communication with a vacuum pump 39 that removes expended coolant from the treatment element (such as a balloon 30, as shown in FIG. 1A). The combination of coolant injection and suction from the vacuum pump 39 forces coolant from the treatment element into the fluid return lumen 37.

Figure 2A:
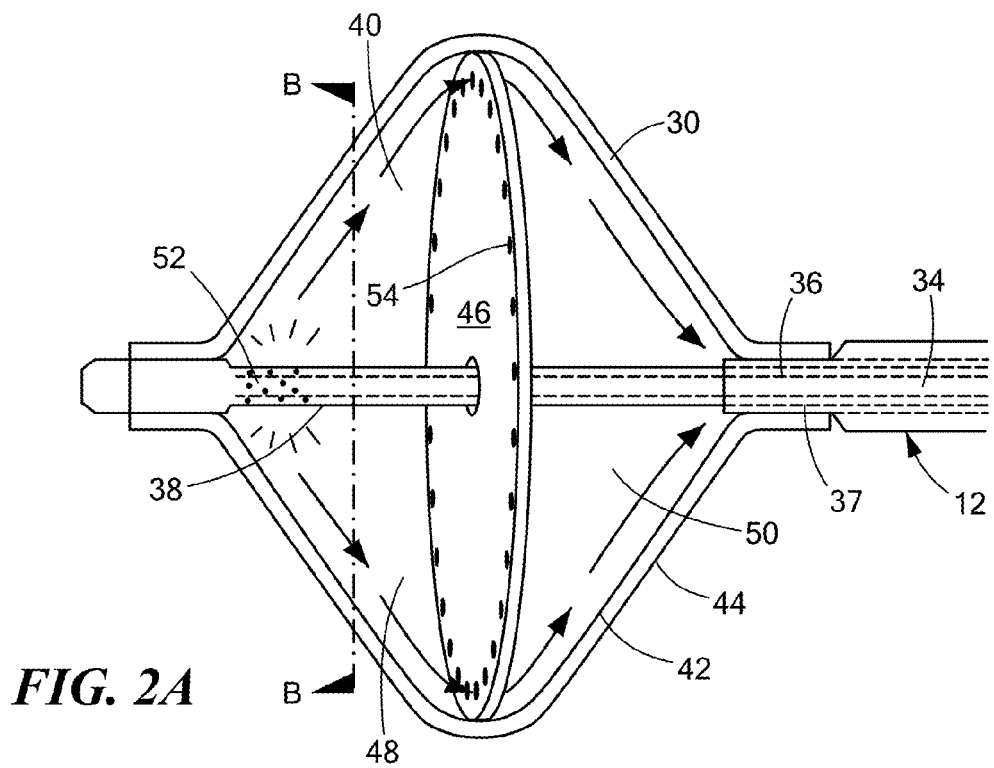
FIG. 2A shows a cross-sectional view of a second embodiment of a cryoablation treatment element.
Figure 8A:
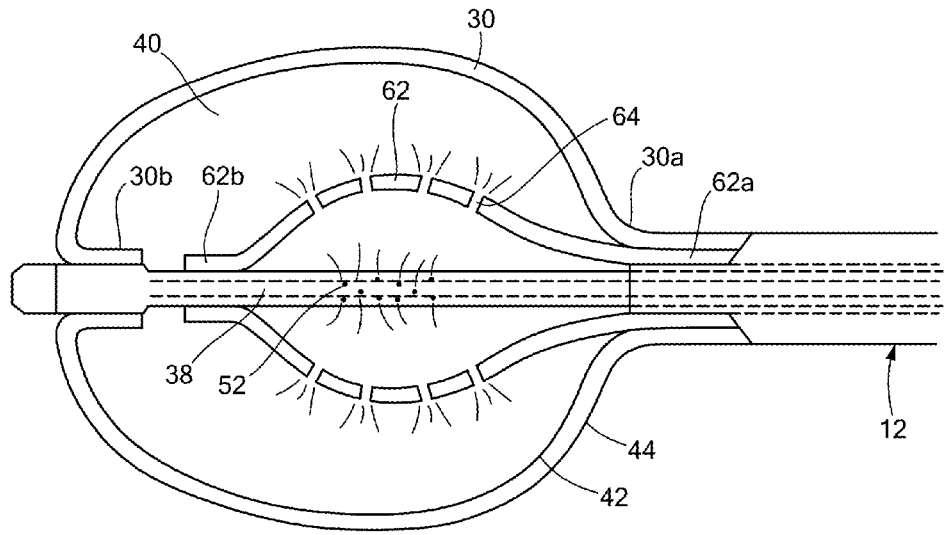
FIG. 8A shows a second embodiment of a shape-changing cryoablation treatment element having a first shape.
Figure 8B:
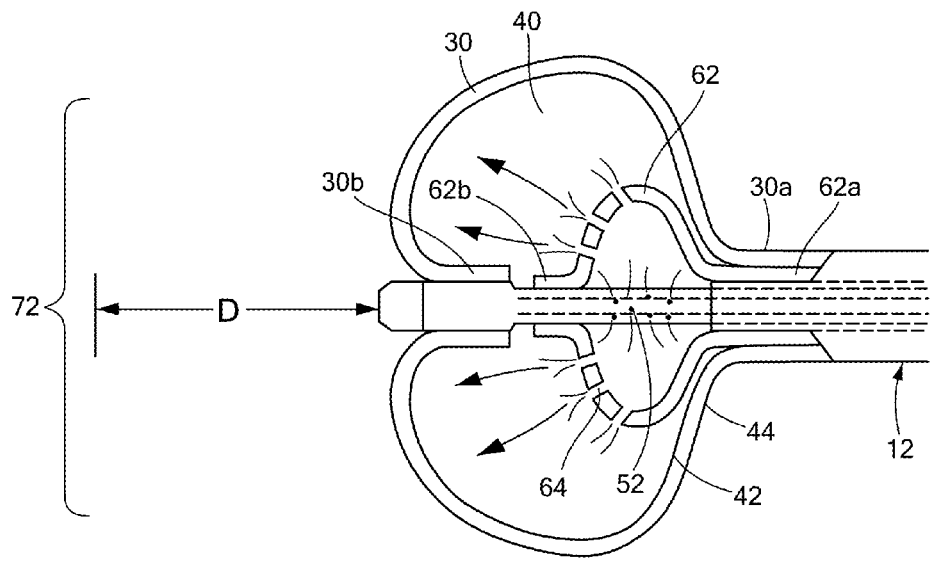
FIG. 8B shows a second embodiment of a shape-changing cryoablation element having a second shape.

Continuing to refer to FIG. 1A, the treatment element may be an expandable element, such as the balloon 30 in FIG. 1A, defining a cooling chamber 40 having an interior wall 42 and an exterior wall 44. The balloon 30 further includes a proximal neck 30a and a distal neck 30b. The balloon 30 further includes a fluid dispersion element (FDE) 46 that directs the flow of coolant from the fluid injection element 46 to the interior wall 42 of the balloon 30, and divides the cooing chamber 40 into a first portion 48 and a second portion 50. A fluid injection element 52 is be disposed within the first portion 48 of the cooling chamber 40, and may be a discrete element (as shown in FIG. 1A) or integrated with the shaft 38 (as shown in FIG. 2A). Additionally, the fluid injection element 52 may be associated with the shaft 38 in a way that allows for an adjustment of the direction of fluid delivery corresponding to the direction and degree of shaft 38 movement (as shown in FIGS. 8A and 8B). Coolant is at its coldest temperature immediately after expanding once it enters the cooling chamber 40; therefore, quickly directing the cold coolant to the area of the cooling chamber closest to target tissue provides a more efficient use of coolant. The FDE 46 shown in FIG. 1A is a deformable membrane oriented perpendicular to the primary direction of coolant flow (depicted in the figures by arrows). The membrane 46 includes a plurality of apertures 54, the apertures 54 being located proximate at least a portion of the interior wall 42. The membrane 46 has a first edge 56 and a second edge 58, the first edge 56 being in contact with the interior wall 42 of the balloon 30 and the second edge 58 being in contact with the shaft 38 and/or the fluid injection element 52. Further, the first edge 56 may be affixed to the interior wall 42 of the balloon 30. The membrane 46 may be between approximately 0.0001 inch and approximately 0.002 inch thick as measured on the first edge 56, and the thickness may be substantially constant throughout the membrane 46, or it may vary. For example, the thickness may be greater near the first edge 56 and lesser near the second edge 58.

Continuing to refer to FIG. 1A, the apertures 54 may be any shape that preserves the integrity of the membrane 46, including circular, angular, flap-like (creating a flap of membrane material that is only partially attached to the membrane 46), or slit-like (an elongated aperture not having a flap of membrane material). Further, the apertures 54 may be located around the entire circumference of the membrane 46 proximate the first edge 56, or only a portion thereof. Further, the apertures 54 may be arranged in a single row, multiple rows, or any other configuration that meters coolant flow from the first portion 48 to the second portion 50 of the balloon 30. The membrane may be composed of a material such as polyester, nylon, Pebax®, polyurethane or silicone, for example. Further, the membrane 46 may be composed of a material that is gas permeable, liquid permeable, or both, or may be permeable to the coolant by virtue of the apertures 54 alone.

Figure 1B:
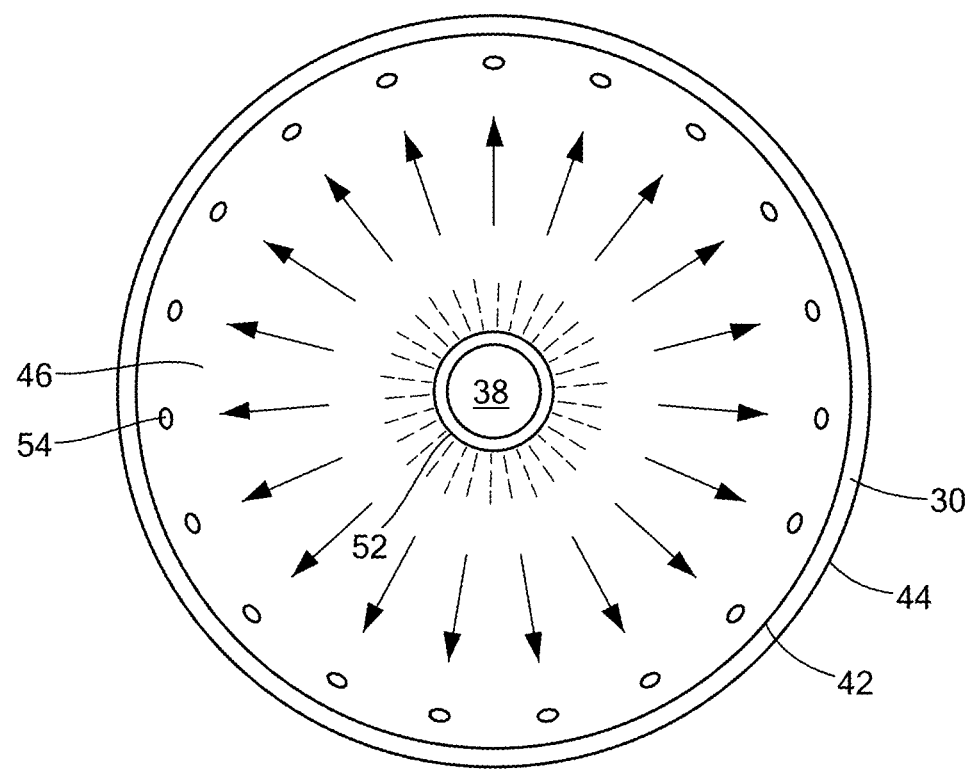
FIG. 1B shows a cross-sectional view of a first embodiment of a cryoablation treatment element.

Referring now to FIG. 1B, a cross-sectional view of a first embodiment of a cryoablation treatment element is shown. FIG. 1B shows the first portion 48 of the cooling chamber 40 as taken along axis B-B in FIG. 1A. As shown and described in FIG. 1A, the balloon 30 defines a cooling chamber 40 (the first portion 48 of the cooling chamber 40 is shown in FIG. 1B) and includes an FDE 46 that is a membrane having a plurality of apertures 54. Coolant is injected into the first portion 48 of the cooling chamber 40 and directed through the apertures 54 of the membrane 46 and into the second portion 50 (not shown in FIG. 1B). The flow of coolant is depicted with arrows.

Figure 2B:
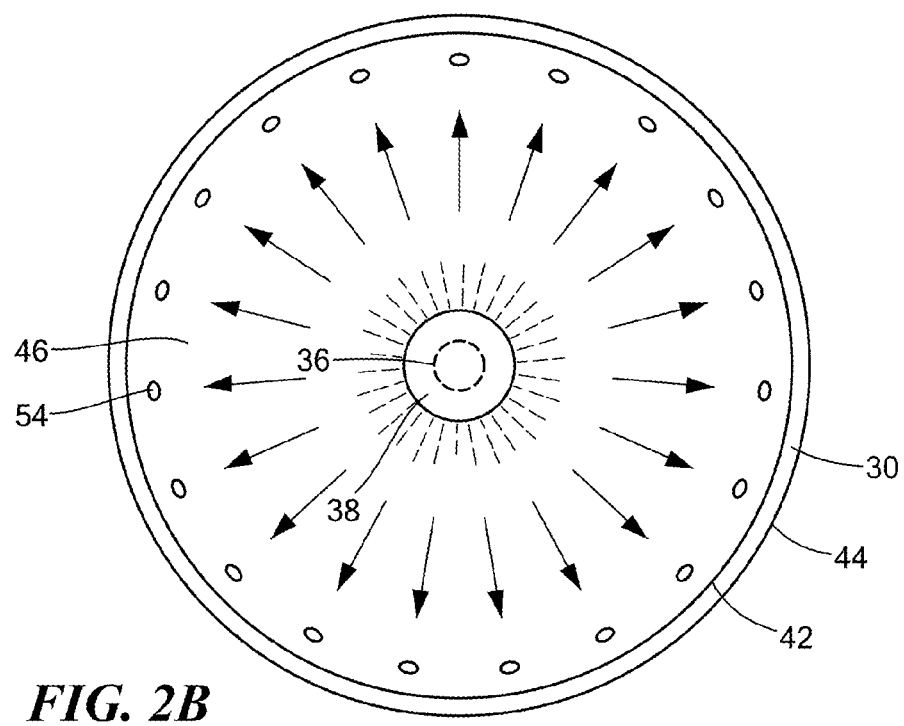
FIG. 2B shows a further cross-sectional view of a second embodiment of a cryoablation treatment element.

Referring now to FIGS. 2A and 2B, cross-sectional views of a second embodiment of a cryoablation treatment element are shown. FIG. 2B shows the first portion 48 of the cooling chamber 40 as taken along axis B-B in FIG. 1A. Like FIGS. 1A and 1B, the treatment element of FIGS. 2A and 2B is a balloon 30 defining a cooling chamber 40 having a first portion 48 and a second portion 50. The balloon 30 further includes an FDE 46 that is a membrane having a plurality of apertures 54. In FIGS. 2A and 2B, the fluid injection element 52 is integrated with the shaft 38, rather than being a separate element disposed about the shaft 38, as shown in FIGS. 1A and 1B. In this embodiment, the fluid injection lumen 36 is within the shaft 38 and the shaft 38 includes a plurality of apertures or outlet ports in fluid communication with the fluid injection lumen 36. Expanded coolant flows from the second portion 50 into the fluid return lumen 37. The cross section shown in FIG. 2B is along the B-B axis shown in FIG. 2A. The flow of coolant is depicted with arrows.

Figure 3:
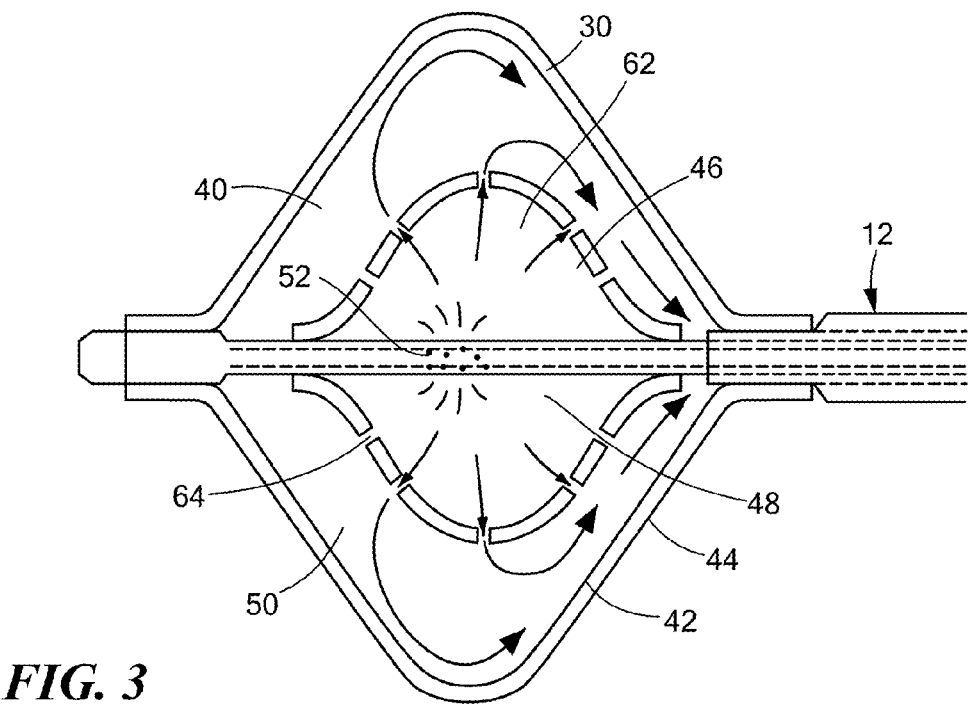
FIG. 3 shows a cross-sectional view of a third embodiment of a cryoablation treatment element.

Referring now to FIG. 3, a cross-sectional view of a third embodiment of a cryoablation treatment element is shown. Like FIG. 1A, the treatment element of FIG. 3 is a balloon 30 defining a cooling chamber 40 and having an interior wall 42 and an exterior wall 44. The balloon 30 further includes an FDE 46 disposed within the cooling chamber 40, dividing the cooling chamber 40 into a first portion 48 and a second portion 50. Unlike the membrane 46 of FIG. 1A, the FDE 46 of FIG. 3 is not in contact with the interior wall 42 of the balloon 30. Rather, the FDE 46 in FIG. 3 is a second balloon 62 of smaller size than the balloon 30 ("first balloon 30"). The second balloon 62 includes a plurality of apertures 64, and the fluid injection element 52 is located within the second balloon 62. The fluid injection element of FIG. 3 is shown as being integrated with the shaft 38 (as shown in FIG. 2A), but could also be disposed about or adjacent to the shaft 38 (as shown in FIG. 1A). The apertures 64 of the second balloon 62 direct and meter flow of coolant from the first portion 48 within the second balloon 62 to the second portion 50 between the first balloon 30 and second balloon 62. Expanded coolant flows from the second portion 50 into the fluid return lumen 37 (as shown in FIGS. 1A and 2A). The flow of coolant is depicted with arrows.

Figure 4:
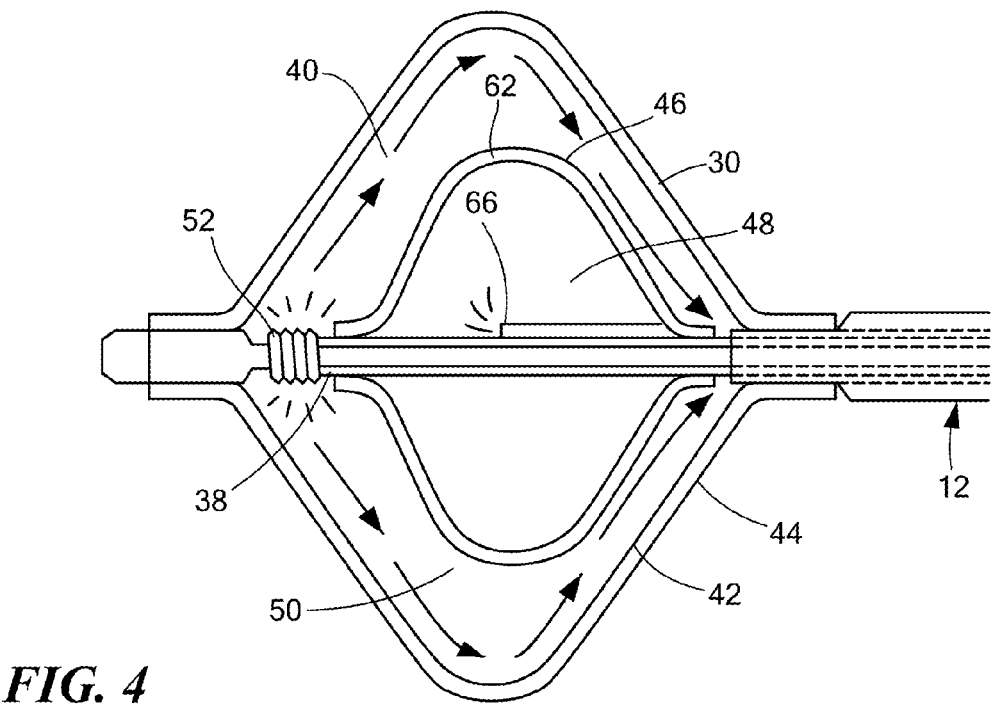
FIG. 4 shows a cross-sectional view of a fourth embodiment of a cryoablation treatment element.

Referring now to FIG. 4, a cross-sectional view of a fourth embodiment of a cryoablation treatment element is shown. Like the treatment element of FIG. 3, the treatment element of FIG. 4 is a balloon 30 defining a cooling chamber 40 and having an interior wall 42 and an exterior wall 44. The balloon 30 further includes an FDE 46 disposed within the cooling chamber 40. Like the FDE 46 of FIG. 3, the FDE 46 in FIG. 4 is a second balloon 62 of a smaller size than the balloon 30 ("first balloon 30"). The fluid injection element 52 is located between the first balloon 30 and the second balloon 62. Further, the second balloon 62 does not meter the flow of coolant from a first portion to a second portion, but does direct the flow of coolant from the fluid injection element 52 to the interior wall 42 of the cooling chamber 40, from where the expanded coolant flows into the fluid return lumen 37 (as shown in FIG. 1A and 2A). The fluid injection element 52 may be a separate element (as shown in FIG. 4) or may be integrated with the shaft 38 (as shown in FIGS. 2A and 3). Further, the second balloon 62 may include a second fluid injection element 66 for inflating the second balloon 62. The flow of coolant is depicted with arrows.

Figure 5A:
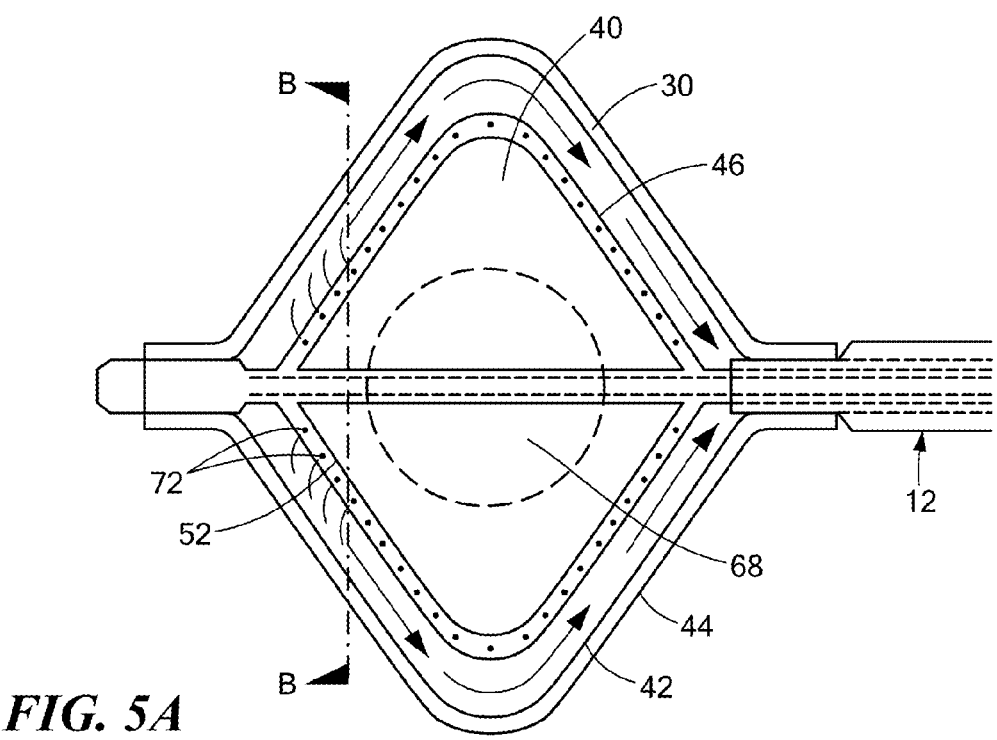
FIG. 5A shows a cross-sectional view of a fifth embodiment of a cryoablation treatment element.
Figure 5B:
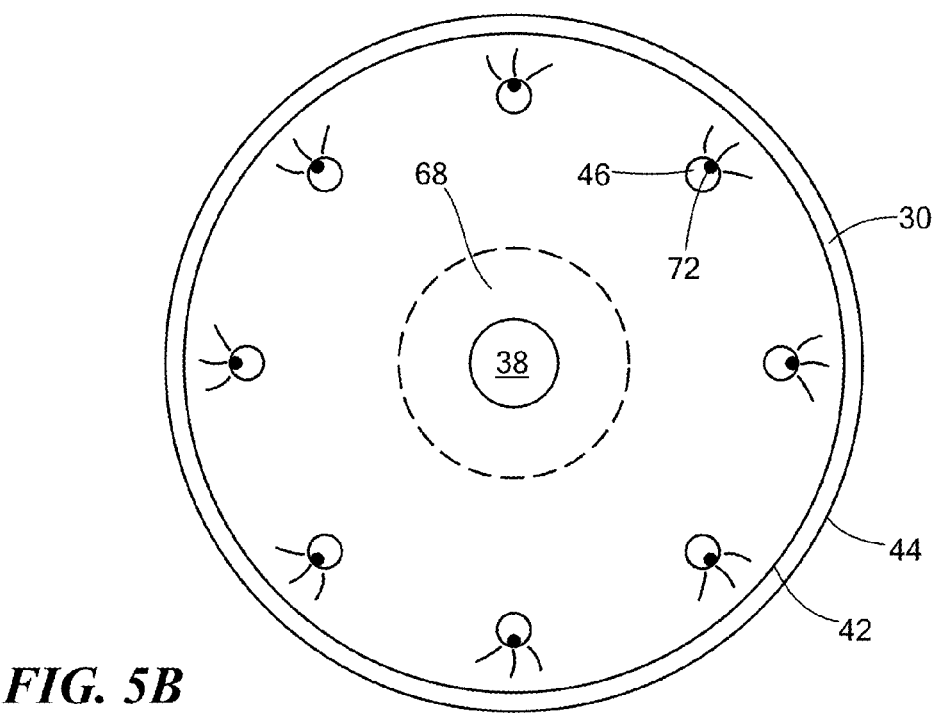
FIG. 5B shows a further cross-sectional view of a fifth embodiment of a cryoablation treatment element.

Referring now to FIGS. 5A and 5B, cross-sectional views of a fifth embodiment of a cryoablation treatment element are shown. FIG. 5B shows the first portion 48 of the cooling chamber 40, as taken along axis B-B in FIG. 1A. Like the treatment element of FIG. 4, the treatment element of FIGS. 5A and 5B is a balloon 30 defining a cooling chamber 40 and having an interior wall 42 and an exterior wall 44. The balloon 30 further includes an FDE 46 disposed within the cooling chamber 40. Like the second balloon 62 of FIG. 4, the FDE 46 of FIGS. 5A and 5B does not meter the flow of coolant from a first portion to a second portion, but does direct the flow of coolant from the fluid injection element 52 to the interior wall 42 of the cooling chamber 40, from where the expanded coolant flows into the fluid return lumen 37 (as shown in FIGS. 1A and 2A). The center portion 68 (general area depicted in dashed lines) of the cooling chamber 40 is substantially bypassed; that is, coolant may flow directly from the fluid injection element 52, to the interior wall 42, to the fluid return lumen 37 without flowing into the center portion 68. Unlike the FDE 46 of FIGS. 1-4, however, the FDE 46 of FIGS. 5A and 5B is also the fluid injection element 52. The FDE 46 may be a collapsible or deformable cage, basket, or mesh being in fluid communication with the fluid injection lumen 36 and having a plurality of outlet ports 72. The outlet ports 72 may be directed toward the interior wall 42 of the cooling chamber 40 (as shown in FIG. 5B), and may be located along the splines 74 of the cage-type FDE 46. Further, the FDE 46/fluid injection element 52 may (as shown in FIGS. 1A, 2A, 3, and 4) or may not (as shown in FIG. 4) be associated with a shaft 38. Expanded coolant flows from the second portion 50 into the fluid return lumen 37 (as shown in FIGS. 1A and 2A). The flow of coolant is depicted with arrows.

It will be understood that a device contemplated herein may include any combination of the features of the embodiments of FIGS. 1-5. Further, the balloon 30 may have any shape or form, and may further be double layered (as in double-balloon catheters) for enhanced safety. Further, the balloon 30 and a second balloon 52 may have the same or different shapes, and may be made of the same or different materials. The figures may not be drawn to scale.

Figure 6:
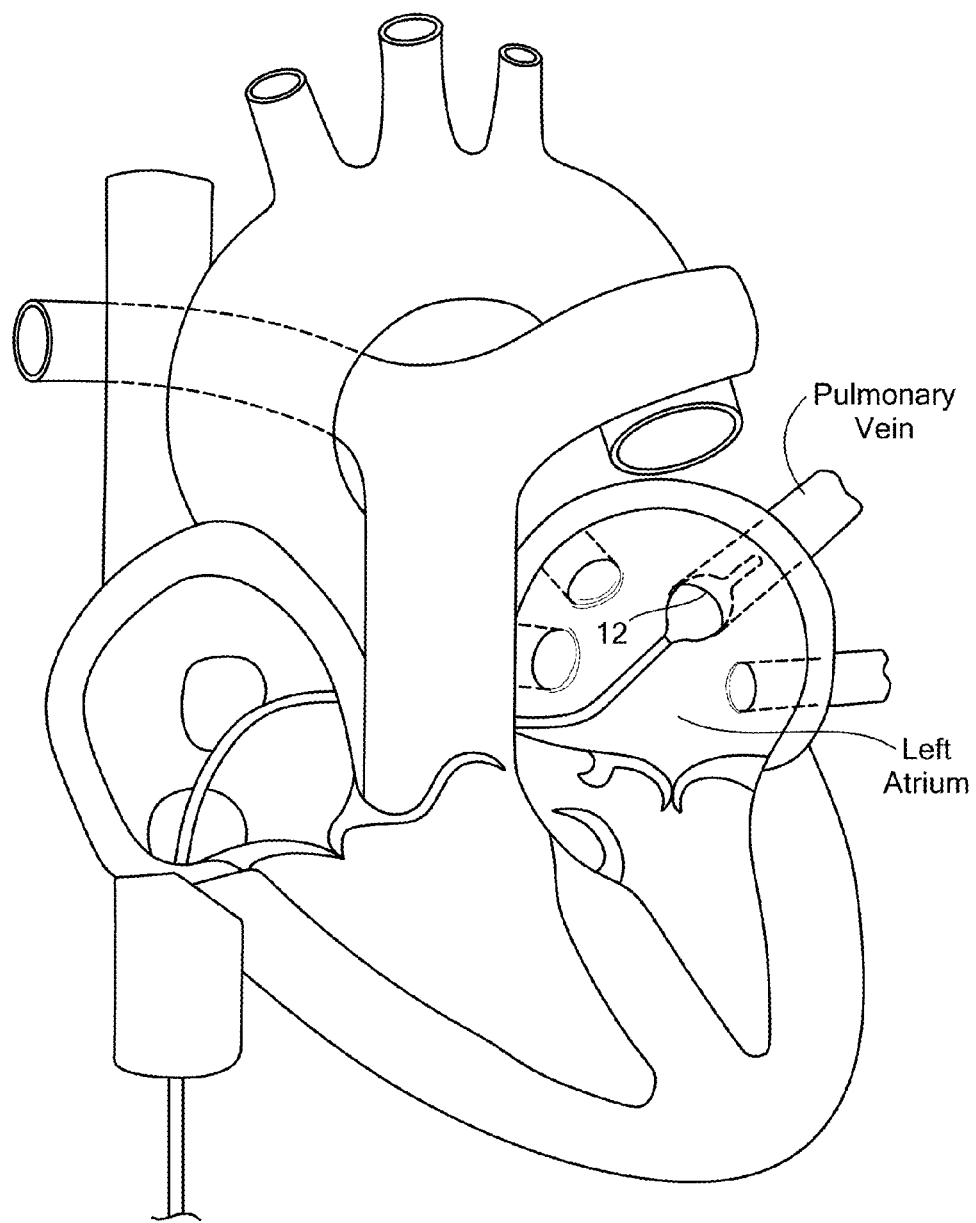
FIG. 6 shows a cross-sectional view of a heart, with exemplary placement of a cryoablation device.

Referring now to FIG. 6, a cross-sectional view of a heart, with exemplary placement of a cryoablation device is shown. A mammalian heart includes pulmonary veins that lead blood from the lungs into the left atrium, and pulmonary vein (PV) ablation is a common treatment for cardiac arrhythmias. In a typical procedure, an ablation device 12 such as a balloon catheter (as shown in FIGS. 1-7) is inserted into the left atrium and positioned at the opening of a PV. Before ablating tissue, a visualization medium (such as a dye or contrast medium) may first be injected into the PV to ensure that the PV is completely occluded by the device 12. Once the occlusion is achieved, ablation may begin. Even though a single balloon catheter having a static shape may provide both occlusion and ablation functionality, it has been found that ablating PV tissue with certain balloon shapes, such as the teardrop or ovate shape in FIG. 7A, may increase the risk of PV stenosis associated with ablation therapy. As shown and described in FIGS. 7A and 7B, the balloons 30 of FIGS. 1-5 may be adjustable from a first shape ("occlusion mode") to a second shape ("ablation mode").

Referring now to FIGS. 7A and 7B, a first embodiment of a shape-changing cryoablation treatment element having a first and second shape is shown. In FIGS. 7A and 7B, the cryoablation treatment element is a balloon 30, which defines a cooling chamber 40 and includes an interior wall 42, an exterior wall 44, a proximal neck 30a, and a distal neck 30b (the balloon 30 may have the general characteristics of any of the balloons 30 of FIGS. 1-5). The proximal neck 30a of the balloon is coupled to the distal end 26 of the elongate body 24, and the distal neck 30b is coupled to the distal end 38b of the shaft 38. Movement of the shaft causes the balloon to assume a first shape ("occlusion mode") or a second shape ("ablation mode"), and all intermediate shapes between the first shape and second shape. When in occlusion mode, the flow rate of the coolant may be lower than that required for ablation. For example, the flow of coolant may be sufficient to inflate the balloon 30, but not enough to reach ablation temperatures.

Referring now to FIG. 7A, a cross sectional view of the balloon 30 having a first shape is shown. In the first shape, the cooling chamber 40 may have an elongated shape, such as a teardrop or ovate shape as shown in FIG. 7A. If the FDE 46 is a membrane oriented perpendicular to coolant flow (as in FIGS. 1-2) as the fluid travels from the first portion 48 to the second portion 50 and into the fluid return lumen 37, the first portion 48 of the cooling chamber 40 may be extended to accommodate the shape change as shown and described in FIG. 7B. The distal neck 30b may be coupled to the distal end 38b of the shaft 38 such that the distal neck 30b is directed outward (as shown in FIGS. 7A and 7B). That is, the interior wall 42 of the distal neck 30b is coupled to the distal end 38b of the shaft 38. However, the distal neck 30b may alternatively be directed inward, with the exterior wall 44 of the balloon 30 coupled to the distal end 38b of the shaft 38 (as shown in FIGS. 8A and 8B). Further, the shaft 38 may be slidably movable within the main lumen 34 of the elongate body 24 (depicted with a double-headed arrow).

Continuing to refer to FIG. 7A, the balloon 30 may further include one or more sensors 70. The sensors 70 may be used to detect pressure, temperature, or other detectable parameters within the system 10, device 12, or patient's body. The sensors 70 may be located anywhere within or on the surface of the balloon 30, but at least one sensor 70 may be located such that movement of the shaft 38 will also effectively reposition the sensors 70. For example, the sensors 70 may be located a distance away from the distal end 38b of the shaft 38 when the balloon 30 is in the first position (as seen in FIG. 7A). As the balloon 30 transitions from the first position to the second position (and the distal end 38b of the shaft 38 is moved closer to the elongate body 24), the sensors 70 will be brought closer to the distal face 72 of the balloon 30 (as shown in FIG. 7B). The distal face 72 is shown as the bracketed area in FIG. 7B.

Referring now to FIG. 7B, a cross-sectional view of a shape-changing cryoablation treatment element having a second shape is shown. The balloon of FIG. 7B is in the second shape, or ablation mode. When in ablation mode, the flow rate of the coolant may be increased so that the balloon 30 reaches a temperature sufficient to ablation tissue. To change the balloon 30 to the second shape, the shaft is retracted a distance ("D") within the main lumen 34. Moving the shaft 38 also moves the position of the distal neck 30b of the balloon 30, which may cause the distal neck 30b to be retracted inward and the distal end of the balloon 30 to fold over on itself. The distal neck 30b may be coupled to the distal end 38b of the shaft 38 in other ways, such as folded under (with the exterior wall 44 of the balloon 30 coupled to the distal end 38 of the shaft); however, the method of affixing the balloon 30 to the shaft 38 should not hinder the shape-changing functionality of the device 12.

Continuing to refer to FIG. 7B, the one or more sensors 70 are on the distal face 72 of the balloon 30 when the balloon 30 is in the second position. On the distal face 72, the sensors 70 may be in an optimal position to contact surfaces within the patient's body and/or to measure parameters detectable by the sensors.

Referring now to FIGS. 8A and 8B, a second embodiment of a shape-changing cryoablation element having a first and second position is shown. Like FIGS. 7A and 7B, the cryoablation treatment element is a balloon 30 ("first balloon"), which defines a cooling chamber 40 and includes an interior wall 42, an exterior wall 44, a proximal neck 30a, and a distal neck 30b (the first balloon 30 may have the general characteristics of any of the balloons 30 of FIGS. 1-5). The proximal neck 30a of the first balloon 30 is coupled to the distal end 26 of the elongate body 24, and the distal neck 30b is coupled to the shaft 38 either at or proximate the distal end 38b). Unlike the distal neck 30b of the balloon 30 shown in FIGS. 7A and 7B, the distal neck 30b of the first balloon 30 in FIGS. 8A and 8B may be oriented inward, with the exterior wall 44 of the balloon being coupled to the distal end 38b of the shaft 38. Movement of the shaft causes the balloon to assume a first shape ("occlusion mode") or a second shape ("ablation mode"), and all intermediate shapes between the first shape and second shape.

Referring now to FIG. 8A, a cross sectional view of the balloon 30 having a first shape is shown. The first balloon 30 may include an FDE 46 that is a second balloon 62 (as shown in FIG. 4) having a proximal neck 62a and distal neck 62b, in which the fluid injection element 52 is located. The second balloon 62 may direct coolant in any of a variety of directions, depending on the movement of the shaft 38. The second balloon 62 may include a plurality of apertures 64 through which coolant is injected into the cooling chamber 40. As shown in FIGS. 8A and 8B (and in contrast to FIGS. 3 and 4), the proximal neck 62a of the second balloon 62 may be coupled to the distal end 26 of the elongate body 24, like the proximal neck 30a of the first balloon 30. The proximal neck 30a of the balloon may be in contact with and coupled to the proximal neck 62a of the second balloon 62, the distal end 26 of the elongate body 24, or both. Further, the distal neck 62b of the second balloon 62 may be coupled to the shaft 38, like the distal neck 30b of the first balloon 30. Thus, movement of the shaft 38 may not only affect the shape of the first balloon 30, but also of the second balloon 62. As shown in FIG. 8A, when the first balloon 30 is in the first position, the coolant may be directed through the second balloon 62 in directions substantially perpendicular to the shaft 38 (that is, toward areas the interior wall 42 of the first balloon 30 that are not at the distal face 72 of the balloon 30). Referring now to FIG. 8B, a cross sectional view of the balloon 30 having a second shape is shown. To change the balloon 30 to the second shape, the shaft is retracted a distance ("D") within the main lumen 34 (as shown in FIG. 7B). Moving the shaft 38 also moves the position of the distal neck 30b of the balloon 30, which may cause the distal neck 30b to be retracted inward. Because the distal neck 30b of the balloon 30 is directed inward, the distal neck 30b may not fold over on itself as shown in FIG. 7B, where the distal neck 30b is directed outward. As the shaft 38 is retracted within the main lumen 34 of the device 12, both the first balloon 30 and second balloon 62 are changed to a second shape. When the balloon 30 is in the second position, the distal neck 62b of the second balloon 62 is also drawn toward the distal end 26 of the elongate body 24 (as shown in FIG. 8B). Thus, the apertures of the fluid injection element 52 are oriented toward the distal face 72 of the balloon 30 (similar to the way the sensors 70 are moved in FIGS. 7A and 7B). This orientation of the second balloon 62 may ensure more efficient cooling of the distal face 72, which may be in contact with a surface within a patient's body. The second balloon 62 may be any distance from the interior wall 42 of the first balloon 30 that provides sufficient cooling to the distal face 72 of the first balloon 30 in the second position.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. A medical device comprising:
   a cooling chamber including an interior wall and an exterior wall;
   a coolant delivery element disposed within the cooling chamber; and
   a coolant distribution element disposed within the cooling chamber that guides coolant delivered from the coolant delivery element toward the interior wall of the cooling chamber, the coolant distribution element being disposed within the cooling chamber so as to divide the cooling chamber into a distal first portion and a proximal second portion.

2. The medical device of claim 1, wherein the cooling chamber is a balloon.

3. The medical device of claim 2, wherein the coolant distribution element is a deformable membrane, the coolant delivery element being located within the distal first portion and the membrane allowing transit of coolant from the distal first portion to the proximal second portion.

4. The medical device of claim 3, wherein the deformable membrane meters transit of coolant from the distal first portion to the proximal second portion.

5. The medical device of claim 4, wherein the deformable membrane is at least one of:
   gas permeable;
   liquid permeable; and
   combination thereof.

6. The medical device of claim 4, wherein the deformable membrane includes a plurality of apertures.

7. The medical device of claim 6, wherein the apertures are located proximate the interior wall of the cooling chamber.

8. The medical device of claim 4, wherein the deformable membrane includes a first edge and a second edge, the first edge being in contact with a portion of the interior wall of the cooling chamber.

9. The medical device of claim 8, wherein the first edge is affixed to the interior wall of the cooling chamber.

10. The medical device of claim 3, further comprising:
    a first shaft having a proximal end, a distal end, and a first lumen extending therebetween, the proximal neck of the balloon being coupled to the distal end of the first shaft; and
    a second shaft slidably disposed within the first lumen and having a distal end, the distal neck of the balloon being coupled to the distal end of the second shaft.

11. The medical device of claim 10, wherein the second edge of the membrane is in contact with the second shaft, the second shaft being slidably disposed through the membrane.

12. The medical device of claim 10, wherein the second shaft includes the coolant delivery element.

13. The medical device of claim 10, wherein the second shaft is slidably movable with respect to the coolant delivery element.

14. The medical device of claim 10, wherein the balloon has a first shape when the second shaft is in an extended position, and the balloon has a second shape including a distal face when the second shaft is in a retracted position.

15. The medical device of claim 14, wherein the balloon includes one or more sensors selected from the group consisting of: temperature sensors, pressure sensors, and combination thereof.

16. The medical device of claim 15, wherein the distal neck of the balloon is oriented outward and away from the expandable element when the balloon is in the first position.

17. The medical device of claim 15, wherein the distal neck of the balloon is oriented within the cooling chamber when the balloon is in the first position.

18. A medical device comprising:
    a first balloon defining a cooling chamber including an interior wall and an exterior wall;
    a coolant delivery element disposed within the cooling chamber; and
    a coolant distribution element disposed within the cooling chamber that guides coolant delivered from the coolant delivery element toward the interior wall of the cooling chamber, the coolant distribution element being a second balloon disposed within the cooling chamber of the first balloon.

19. The medical device of claim 18, wherein the coolant delivery element is disposed within the cooling chamber so as to divide the coolant chamber into a first portion within the second balloon and a second portion between the cooling chamber and second balloon, and the second balloon meters transit of coolant from the first portion to the second portion.

20. The medical device of claim 19, wherein the second balloon includes a plurality of apertures.

21. The medical device of claim 20, wherein the coolant delivery element is disposed within a second balloon.

22. The medical device of claim 18, wherein the coolant delivery element is disposed between the first balloon and the second balloon, the second balloon being coolant-impermeable.

23. The medical device of claim 18, wherein the first balloon includes a proximal neck and a distal neck, the device further comprising:
   a first shaft having a proximal end, a distal end, and a first lumen extending therebetween, the proximal neck of the first balloon being coupled to the distal end of the first shaft; and
   a second shaft slidably disposed within the first lumen and having a distal end, the distal neck of the first balloon being coupled to the distal end of the second shaft,
   the coolant delivery element being located within the second balloon, the second balloon having a proximal neck and a distal neck, the distal neck of the second balloon being coupled to the second shaft.

24. The medical device of claim 23, wherein the second balloon directs coolant toward the distal face of the balloon when the balloon is in the second position.

* * * * *